(12) United States Patent  (10) Patent No.: US 8,439,050 B2
Tiphonnet  (45) Date of Patent: May 14, 2013

(54) SELF-DISPENSING DENTAL FLOSS APPLICATOR

(75) Inventor: Joel Tiphonnet, Singapore (SG)

(73) Assignee: Joel Tiphonnet, Singapore (SG)

( * ) Notice: Subject to any disclaimer, the term of this patent is extended or adjusted under 35 U.S.C. 154(b) by 173 days.

(21) Appl. No.: 12/682,409

(22) PCT Filed: Oct. 6, 2008

(86) PCT No.: PCT/EP2008/063328
§ 371 (c)(1),
(2), (4) Date: Apr. 9, 2010

(87) PCT Pub. No.: WO2009/047227
PCT Pub. Date: Apr. 16, 2009

(65) Prior Publication Data
US 2010/0229888 A1    Sep. 16, 2010

(30) Foreign Application Priority Data
Oct. 10, 2007  (EP) ................................. 07118180

(51) Int. Cl.
*A61C 15/00* (2006.01)
(52) U.S. Cl.
USPC .......................................... 132/326; 132/324
(58) Field of Classification Search ........... 132/322–329
See application file for complete search history.

(56) References Cited

U.S. PATENT DOCUMENTS

| | | |
|---|---|---|
| 4,586,521 A | 5/1986 | Urso |
| 4,706,695 A | 11/1987 | Urso |
| 5,176,157 A | 1/1993 | Mazza |
| 5,207,773 A | 5/1993 | Henderson |
| 5,217,031 A | 6/1993 | Santoro |
| 5,323,796 A | 6/1994 | Urso |
| 5,423,338 A | 6/1995 | Hodge |
| 5,560,378 A | 10/1996 | Tiphonnet |
| 5,606,984 A | 3/1997 | Gao |
| 5,664,592 A | 9/1997 | Regnier |

(Continued)

FOREIGN PATENT DOCUMENTS

WO    WO2004/084760    10/2004

*Primary Examiner* — Rachel Steitz
(74) *Attorney, Agent, or Firm* — Occhiuti Rohlicek & Tsao LLP

(57) ABSTRACT

A self-dispensing dental floss applicator that has a U-shaped elongated housing (1) with two hollow prongs (4a, 4b) set perpendicularly to the body at one end and a larger opposite end to contain the locking mechanism, the dispensing mechanism, the spool (3) of fresh floss and the spool (18 or 21) of used floss. The locking mechanism composed of a casing (5), an axle (9), two lower grip pads (17a, 17b), two upper grip pads (7a, 7b), two strip springs (8a and 8b) and a lever (6) with two eccentric friction parts is used to hold the floss in position thus creating the right tension on the floss. A tension pin (19) containing a screw (20) is provided to increase floss tension if/when needed by the user. Rotating the lever (6) up unlocks the floss. Further repeated rotations of the lever backward action the sliding mechanism containing a rack-and-pinion gear (23 and 21), together with springs 24 and 26, that in turn causes the spool of used floss (21) to rotate. Hence, new fresh floss is spanned between the prongs. In a separate embodiment, the applicator is placed on the electrical base and pressing it down will cause the spool of used floss (18) to rotate, hence pulling new fresh floss between the prongs in a very fast and easy manner. Pushing back the lever (6) to its locked position ensures the floss is tightly locked with the right tension.

18 Claims, 9 Drawing Sheets

U.S. PATENT DOCUMENTS

| | | |
|---|---|---|
| 5,762,078 A | 6/1998 | Zebuhr |
| 5,769,102 A | 6/1998 | Zebuhr |
| 5,816,271 A | 10/1998 | Urso |
| 7,156,110 B2 | 1/2007 | Landry |
| 7,201,173 B2 | 4/2007 | Shen et al. |
| 7,475,695 B2 | 1/2009 | Filsouf |
| 2004/0255972 A1 | 12/2004 | Chen |
| 2005/0000537 A1 | 1/2005 | Junkins |
| 2007/0000515 A1 | 1/2007 | Yang |
| 2008/0029122 A1 | 2/2008 | Egeresi |
| 2008/0092917 A1 | 4/2008 | Getgey |
| 2008/0289648 A1 | 11/2008 | Liu |
| 2010/0139689 A1 | 6/2010 | Couch |
| 2010/0229888 A1 | 9/2010 | Tiphonnet |

SELF-DISPENSING DENTAL FLOSS APPLICATOR

CROSS-REFERENCE TO RELATED APPLICATIONS

This application is the National Stage of International Application No. PCT/EP2008/063328, filed on Oct. 6, 2008, which claims the benefit of European Patent Application No. 07118180.4, filed on Oct. 10, 2007, the contents of both of the foregoing applications are hereby incorporated by reference in their entirety.

FIELD OF THE INVENTION

The present invention relates to tooth flossing and, more specifically, to a self-dispensing dental floss applicator usable for inserting a string or ribbon of dental floss between two single teeth and cleaning the gap between these teeth by repeatedly moving the floss back and forth and up and down.

BACKGROUND OF THE INVENTION

Dentists recognise dental flossing as a necessary and effective part of teeth cleaning and plaque removing. Flossing is indeed the only effective method for cleaning between the teeth to remove plaque build-up, which is the primary cause of gingivitis, periodontal and tooth decay. For good results, flossing should be performed daily. Beside the related applications of the applicant, today there is not any practical, well-designed device that gives consumers a high level of satisfaction with regard to usage, hygiene, etc. Finger flossing continues to be the most common method used by people even though it is primitive and does not provide good results especially for the rear teeth.

A dental floss applicator is known from EP 0 661 026 B1. According to EP 0 661 026 B1 a self-dispensing dental floss applicator is known revealing a generally U-shaped housing, having a space for a spool of floss at its one end and two hollow prongs extending parallel to each other at its other end, the floss being spanned between the free ends of the prongs and passed from the spool through a locking mechanism, a guiding section, the hollow prongs back to the guiding section and the locking mechanism wherein the locking mechanism consists of a casing, rotatably mounting a lever with double eccentric acting on two grip pads and a grip pad spring provided between said grip pads and said casing. The self-dispensing dental floss applicator known from the prior art needs the power of the fingers of the user to move the floss and is therefore less comfortable and moves the floss very slowly. Furthermore the used floss has to be cut by the user and therefore the applicator known from the prior art is less hygienic in use.

Document WO 2004/084760 A2 discloses a dental floss applicator, wherein dental floss is guided from a first spool, located in a housing, over two prongs back to the housing, where the used floss is collected on a second spool. The tension that is applied to the floss can be adjusted be the user by engaging a stop pin that stops floss from the supply spool being pulled towards the prongs and then manually turning the second spool.

Document U.S. Pat. No. 5,060,681 A discloses a dental floss applicator, wherein dental floss is guided from a first spool, located in a housing, over two prongs back to the housing, where the used floss is collected on a second spool. The tension that is applied to the floss is maintained at a constant value by means of a tapered spool and a rack and pinion locking mechanism.

Document U.S. Pat. No. 5,188,133 A discloses a dental floss applicator, wherein dental floss is guided from a first spool, located in a housing, over two prongs back to the housing, where the used floss is threaded through a locking mechanism and then further out of the housing through an exhaust channel. A fixed tension is applied to the floss by a spring-loaded locking mechanism.

SUMMARY OF THE INVENTION

It is an object of the invention to create a self-dispensing dental floss applicator mitigating the disadvantages of the prior art and being easy to handle and less expensive in production.

The above mentioned problems will be solved by a self-dispensing dental floss applicator according to claim 1 with a generally u-shaped housing having a space for a spool of floss at its one end and two hollow prongs at its other end, the floss being spanned between the free ends of the two prongs and passed from the spool through a locking mechanism, a guiding section, the hollow prongs back through the guiding section and the locking section, wherein the housing contains a second spool and that the first spool contains the fresh floss and that the second spool is for accumulating the used floss, wherein the second spool contains a gear wheel to drivingly connecting the gear wheel with a drive unit.

According to the invention it is advantageous that the gear wheel meshes a rack with gear teeth slidingly accommodated in a cavity of the housing.

Furthermore, it is helpful that the rack is in connection with a shaft, which can be easily operated with a lever.

According to another embodiment of the invention it is of advantage that the rack is biased by a spring, such that the spring exercises a longitudinal force along its axis pushing the rack forward. The spring is preferably a spiral spring or another type of spring.

Furthermore, it is of advantage that the shaft and the rack are connected by another spring-type element or spring element.

According to another embodiment of the invention, it is of advantage that the housing of the applicator contains an opening in the rear end of the housing allowing a driving gear wheel to be at least partly introduced through the opening to mesh the gear wheel within the housing.

Furthermore, it is of advantage that the driving gear wheel is part of a base element. According to another embodiment it is of advantage that the base element contains an electric motor, at least one battery and a switching element to start or stop the electric motor. Instead of a battery another power supply means may be provided too.

According to another inventive embodiment, it is helpful that the switching element is a micro switch being easily operated by introducing the rear end of the applicator in a recess of the base.

Furthermore, it is of advantage that the base comprises a guiding element like a positioning groove which is in operational connection with an element of the housing of the applicator.

BRIEF DESCRIPTION OF THE DRAWINGS

The above and other features and advantages of the invention will be apparent from the following description of an exemplary embodiment of the invention with reference to the accompanying drawings, in which.

DETAILED DESCRIPTION OF THE DRAWINGS

Figure 1:
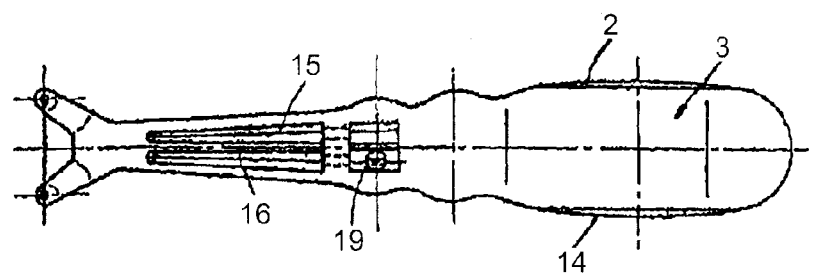
FIG. 1 shows different views of an inventive floss dispensing applicator.
Figure 1:
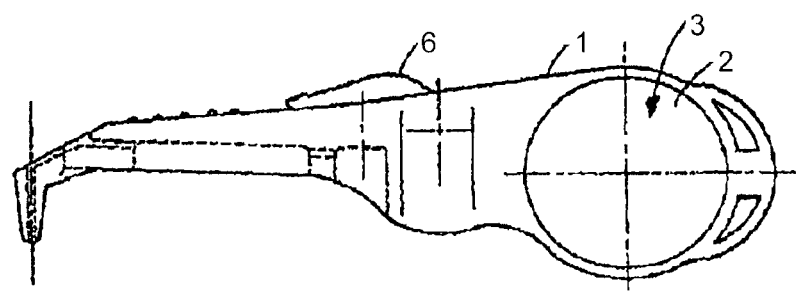
Figure 1:
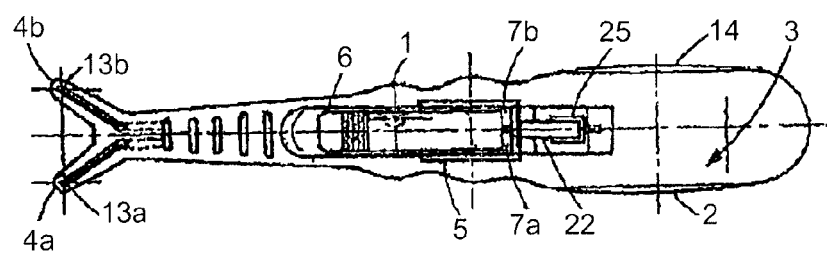
Figure 2:
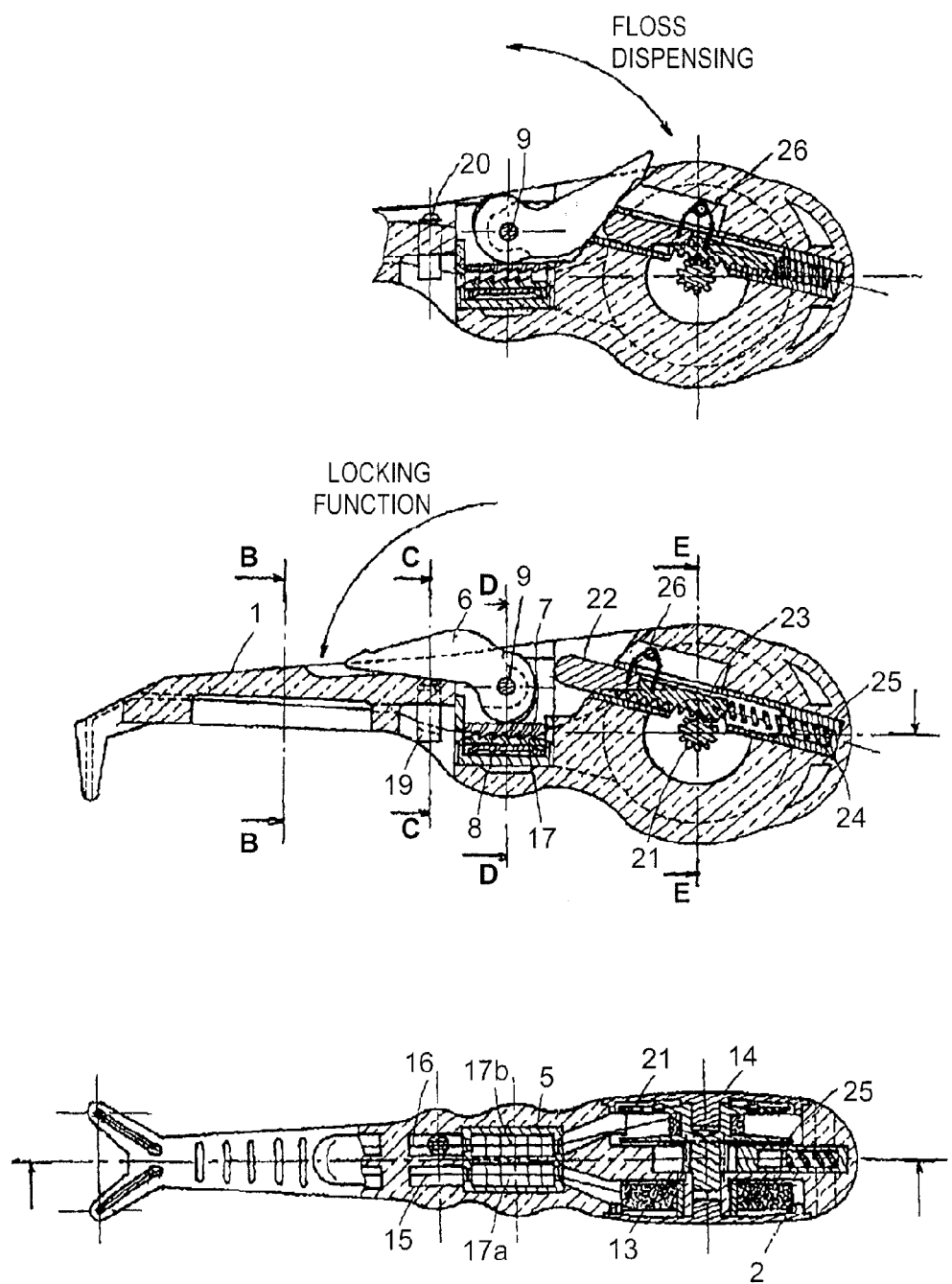
FIG. 2 shows different sectional views of a first embodiment of the inventive applicator.

FIG. 1 and FIG. 2 both show different views of an inventive floss dispensing applicator. The applicator consists of a housing 1, which is preferably u-shaped and made of plastic material. The housing 1 allows performing flossing in the most practical and user friendly way and especially with easy reach of the rear molar teeth. At the rear end of the housing there is a spool 3 arranged to provide fresh floss. This spool 3 may be removed and exchanged if the fresh floss is fully used and therefore the fresh floss spool is empty. The spool 3 is located in a section of the housing which is covered by the cap 2. The cap 2 protects and holds the spool 3 in position.

At the front end of the housing 1 there are two hollow prongs 4a, 4b arranged to provide a predetermined floss tension for flossing. The floss is fed through the prongs and kept under tension. Especially the floss is fed from the spool 3 through one of the prongs 4a, 4b to the second prong 4b, 4a to a used floss spool.

In the prongs are borings 13a, 13b located to maintain floss in position and to keep the tension of the floss while the floss is feed through the borings 13a, 13b. The prongs are arranged in an angle of about 90° or less and the borings 13a, 13b are arranged accordingly in an angle relative to each other.

Within the housing there is a locking casing 5 which houses a locking mechanism of the made of a lever 6 an axle and grip pads 7, 17 and springs 8. The core elements are quickly removed by pulling them out of the housing 1 in vertical direction.

The lever 6 is designed as a double eccentric lever to provide locking and tension of the floss. Additionally the lever 6 is a dispensing actor in a mechanical version of the applicator. As can be seen in FIG. 1, the lever 6 is located at least partly in the housing 1 and consists of a part not located in the housing.

The grip pads 7, 17 are divided in lower grip pads 17a, 17b and upper grip pads 7a, 7b. The both types of grip pads are designed to exercise pressure on floss under rotation of lever 6 and action of spring 8. The grip pads are made of metal or of plastic material. The grip pads 7, 17 both contain saw teeth pattern.

The spring 8 is made of metal or of e.g. plastic material and is located below the lower grip pads. The spring 8 is made as curved strip spring.

The lever axle 9 is preferably made of metal or plastic material and keeps the lever 6 in a defined position and allows the lever 6 to turn around the axle 9.

Figure 4:
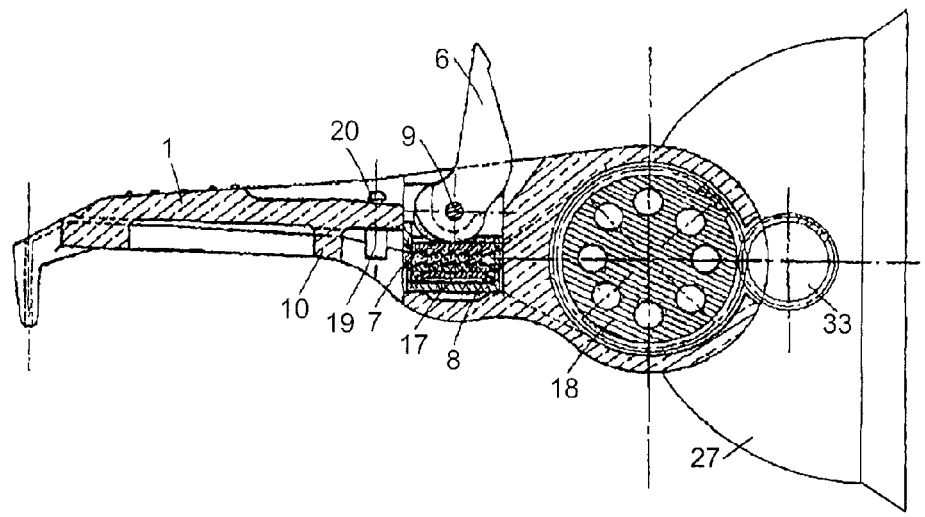
FIG. 4 shows details of a second embodiment of the inventive applicator.
Figure 4:
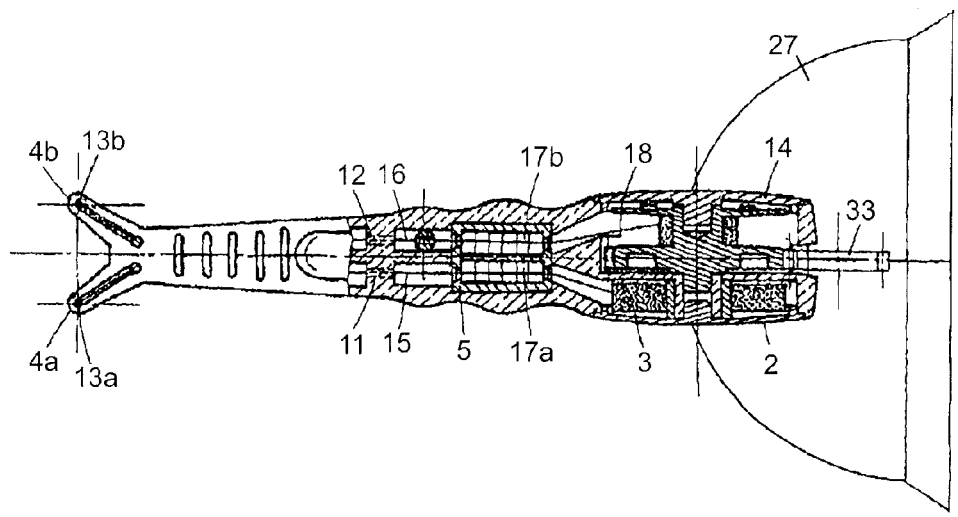

FIG. 1 shows the guiding partition in the view from below situated at the top of FIG. 1. Similarly they can be seen on FIG. 2. FIG. 4 shows additionally guiding partitions 10 inside the housing 1 which can be provided in the housing of FIG. 1 or 2 too, but they are not seen. The guiding partitions are used to guide the floss from the fresh floss spool to the bores 13 or from the bores 13 to the used floss spool. Reference sign 11 denotes a bore to guide fresh floss from the locking mechanism to the bore 13a, while reference sign 12 denotes a bore to guide used floss from the bore 13 to the used floss spool or to locking mechanism. As can be seen in FIG. 4, the bores 11 and 12 are almost parallel and they are located between the lever 6 mechanism and the prongs 4. In FIG. 4 the fresh floss 15 is shown while the used floss 16 is shown too. Both the fresh and the used floss are almost parallel within the housing 1 and the fresh floss 15 is spanned between the prongs 4a, 4b to allow the flossing. The used floss is floss already used which will be reeled on a used floss spool 18 or 21.

The used floss spool 18 is located in the housing 1 and covered by the cap 14 which protects and holds the spool and gear within the housing 1. The spool 18 contains the used floss which is reeled and the spool contains a large gear, which goes in rotary motion when the floss is dispensed in the electrical version of the applicator.

As can be seen in FIG. 4, the applicator may contain an additional tension pin 19 and an adjustable screw 20 to increase the floss tension and to provide additional floss tension. FIG. 2 shows the used floss spool 21 with a small gear wheel which is going into rotary motion when the floss is dispensed. Additionally to the spool with the small gear wheel the applicator contains a mechanism to drive the gear wheel 21. This mechanism contains a shaft 22 which transmits a linear movement of the shaft into a rotational movement of the gear wheel 21. The shaft is therefore provided with gear teeth in linear arrangement as can be seen as rack 23. In case the shaft is moved linear the gear wheel 21 is turned around the axis of the gear wheel. As can be seen the shaft 22 transmits movement of the rotating lever 6 to the rack 23. The rack is part of the rack-and-pinion-gear device to transmit a linear movement into a rotational movement. Since the rack is moving against the force of the spring 24, the spring 24 is able to actuate the rack 23 accordingly. The spring 24 is realised as cylindrical spring but can be realised as other type of spring if necessary. The spring provides a required pressure on rack 23 to push the rack back in starting position when the lever 6 is rotated forward to lock the floss between the grip pads 7, 17.

When the lever 6 is rotated backward the floss will be dispensed and when the lever is rotated forward the floss dispensing mechanism will be stopped.

According to FIG. 2 the housing 1 contains a dispensing mechanism casing 25, which is the rear part of the housing 1 of the applicator. The casing 25 houses the shaft 22 the rack 23 and the spring 24. Therefore, the casing can be designed as having a longitudinal hollow bore containing the above mentioned parts 22 to 24. According to another embodiment of the invention, the casing can be installed in a cavity of the housing 1 of the applicator, preferably before the spool 21 is installed in the housing 1 and maintained in position by cover 14.

According to FIG. 2, the shaft 22 and the rack 23 are movable relative to each other. Both elements 22 and 23 have a sliding surface with which both elements can slide relatively to each other. A spring 26 is provided between shaft 22 and rack 23 to allow shaft 22 to remain in position in the casing 25 while the rack is free to slide. The spring may have a second function such that the spring 26 pushes the rack back in the upper position such that the rack frees itself from the teeth of the gearwheel 18 when going back in its resting position, what can be seen in FIG. 3.

Figure 5:
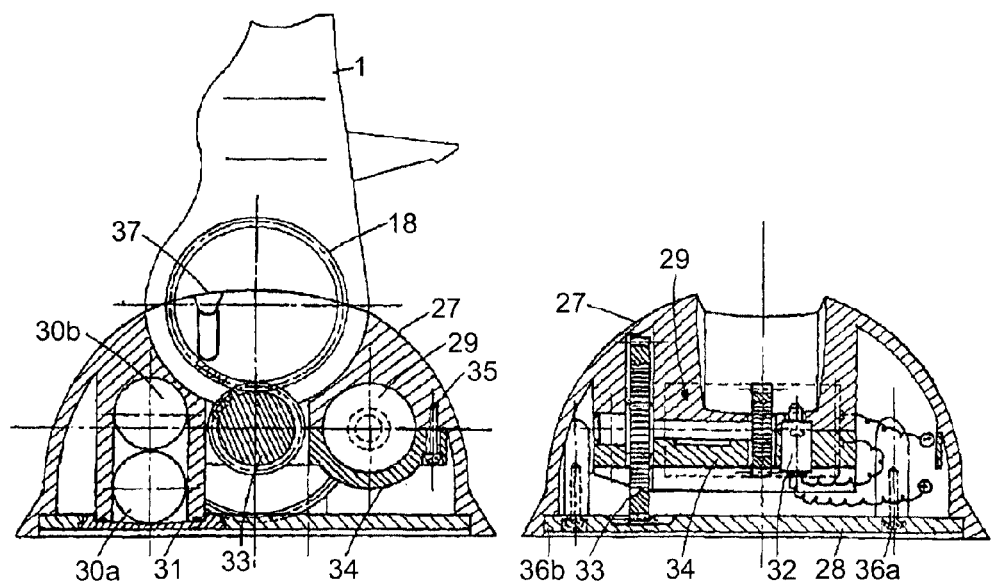
FIG. 5 shows details of the second embodiment of an inventive applicator.
Figure 5:
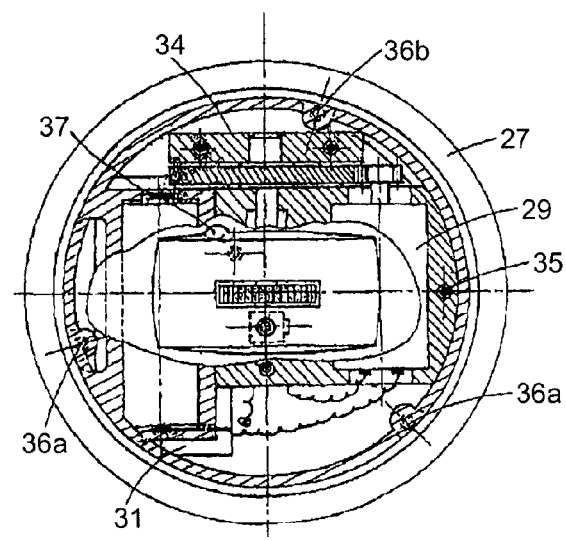

The second embodiment of the FIGS. 4 and 5 is provided with an electrical base 27. The base 27 is preferably a molded plastic part including a recess for the reception of the applicator or of at least the rear end of the applicator. The base comprises an element to allow a stable positioning of the base, i.e. a socket.

As can be seen in FIG. 4, the applicator can be positioned such that the rear end of the housing 1 is accommodated within the base 27. Within the housing there is an opening such that a gear wheel 33 can protrude through this opening to mesh the gear wheel 18 of the applicator. The gear wheel 33 is part of the base 27.

According to FIG. 5, the base 27 includes a base cover 28 which closes the bottom of the almost semi-spherical base 27. The base cover is almost flat and allows a tight closure of the base.

Preferably the closure is watertight. The cover is preferably made of plastic material. The fixation of the base cover 28 can be done using three screws 36a, 36b, 36c or with other fastening means.

Within the base is an electrical motor 29 provided. Preferably the electric motor 29 is a low voltage DC-motor, e.g. a 1.5 V DC-motor. At the drive shaft of the motor 29 is a gear wheel provided which meshes an other gear wheel in driving connection. This double gear wheel can be seen in FIG. 5 and is denoted by reference sign 33. The double gear wheel allows the driving connection between the electric motor and the gear wheel 18. The electric motor is connected via electrical leads with a power supply, e.g. with batteries. As power supply two batteries 30a, 30b are shown which are e.g. alkaline batteries of the disposable type or accordingly batteries of the rechargeable type. The batteries 30a, 30b may be of 1.5 V type. According to FIG. 5 the batteries 30a, 30b are parallel aligned and are positioned above each other. According to FIG. 5, the batteries are disposed in a battery storage room which is closed by a battery cover 31, which can be of the clip-on type. This cover 31 protects and holds the batteries in their cavity inside the base 27. To operate the electric motor a micro switch 32 is provided to switch the electric motor on or off. Preferably the micro switch 32 will be activated when the applicator is inserted in the cavity of the base and is pressed downward in the direction of the base. Accordingly the micro switch is adjusted to receive the rear part of the applicator when the applicator is inserted in the cavity of the base and switches the electric motor on.

Within the base is at least one holding part 34 or a holding strap which holds the elements 29, 32 and 33 in place. This holding element can be a molded part of plastic material. The holding part or strap is fastened with fastening means, e.g. fastening screws 35. According to the shown embodiment five screws are used to fasten and hold the strap 34 in position inside the base 27. Furthermore, fastening means 36 are used to hold the base cover 28 in position and to fasten the base cover. According to the shown embodiment of FIG. 5 three screws are used as fastening means 36.

Additionally, as can be seen in FIG. 5, a positioning groove 37 is provided in the base which co-operates with a positioning element of the applicator to allow the applicator to be placed properly within the base during a dispensing action.

Figure 3:
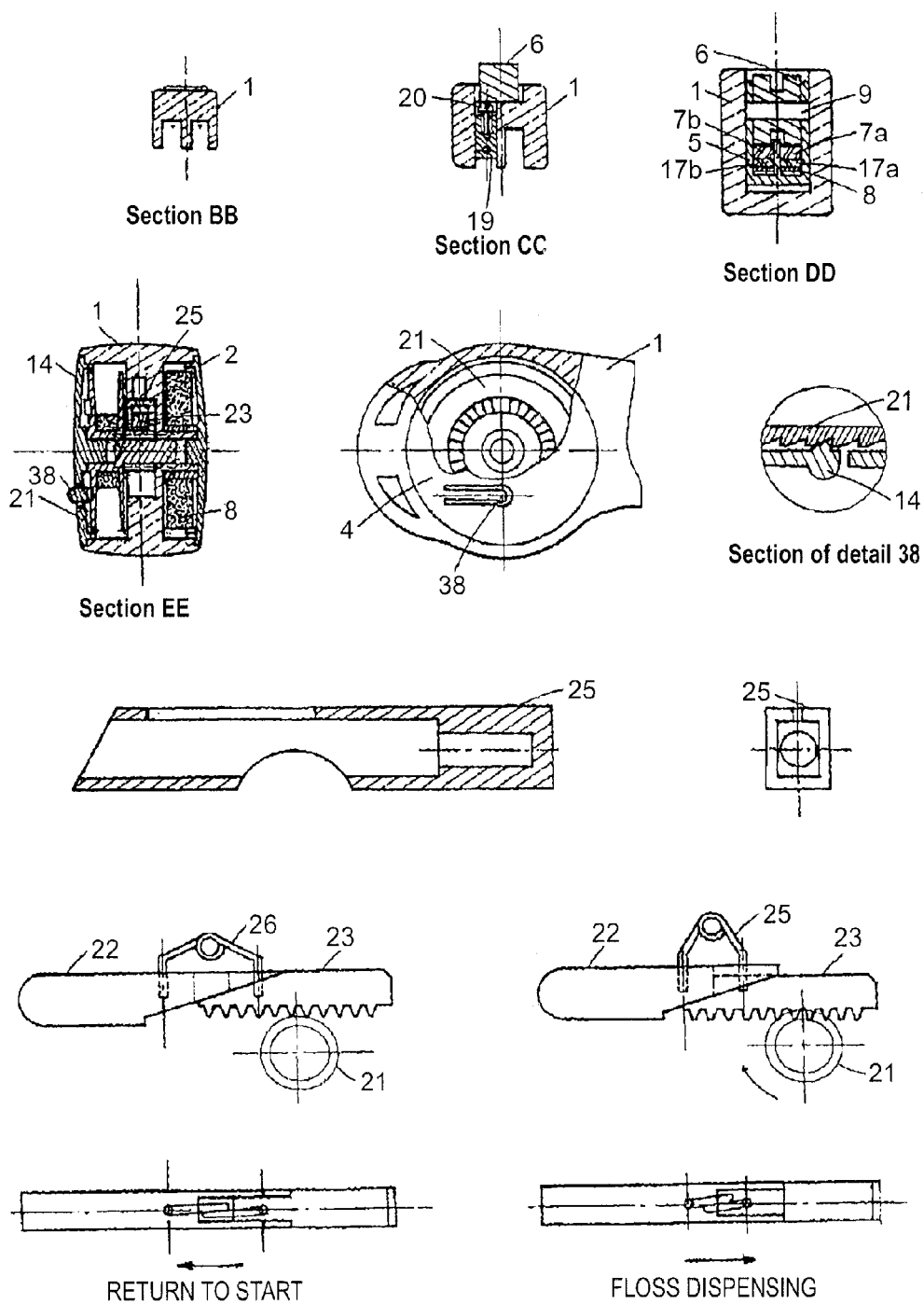
FIG. 3 shows details of the first embodiment of the inventive applicator.

Additionally, as can be seen in FIG. 3, an anti-return device 38 is provided which prevents spool 18 and/or 21 to rotate back after it has been in rotary motion to reel used floss on wheel and hence dispensed new fresh floss between the prongs. Therefore, the anti-return device is a flexible element with a teeth portion which co-operates with a teethed portion of a wheel 18 and/or 21 to allow only a rotation in one direction of the wheel.

According to the invention, the applicator allows a floss locking mechanism. The presence of two curved strip springs 8a, 8b placed underneath the lower gripping pads 17a, 17b ensures that the pressure exercised by the gripping pads 7, 17 on the floss is almost constant independent of the floss characteristics or floss materials e.g. Nylon or Teflon, string or ribbon, waxed or non-waxed and thickness tolerances are.

Furthermore, a thin partition in the casing 5 of the locking mechanism between the fresh floss and used floss ensures that no direct contact exists between the two paths for fresh and used floss.

Therefore there is no direct contact between fresh floss and used floss in any part of the applicator making it extremely hygienic. Furthermore, floss spools, both fresh 3 and used floss 18 or 21 are located in two separate closed compartments of the applicator. There is no direct contact with any part of the human body (mouth or hand). The fact that used floss is isolated in a confined environment is a positive factor.

After each use of the applicator, the user is asked to wash the frontal part of the applicator, i.e. the prongs and the spanned floss under the tap before a new part of floss is dispensed between the prongs. This practice means used floss is relatively clean before being stored in its spool.

According to an inventive embodiment, a change in tightness of floss is possible. Should the user wants to obtain a tighter floss beyond what the mechanism already provides, he just needs to unscrew the little screw 20 which will receive downward pressure from the lever 6 when this one is in final locked position. As such, extra pressure will be exercised on the used floss string 16 from pin 19 as it passes through it.

The introduction of the dual function of the lever in the mechanical version of the self-dispensing dental floss applicator is generally favourable. The mechanical version of the inventive self-dispensing dental floss applicator according to FIGS. 1 to 3 relies on finger power to obtain floss dispensing. It is a lower cost and slower version of the electrical model described according to FIGS. 4 and 5 yet it performs the same function. The double eccentric lever 6 continues to play a floss locking role.

For ease of use, the action to lock the floss is by pressing forward lever 6 with the thumb and unlock by pulling it backward with the index finger. When the lever 6 reaches almost 45 degrees forward, the fresh floss is locked between the gripping pads 7a and 17a while the used floss will be locked completely between the gripping pads 7b, 17b as the lever 6 is pressed down completely. The added feature of the extra tension pin 19 allows creating more tension on the floss if/when required by the user.

The lever plays also the added role of floss dispenser. By pulling the lever 6 backward with the index finger, a shaft 22 in the sliding mechanism is moved backward and the rack-and-pinion gear system 23 and 21 generates a rotary motion of the used floss spool 21. Hence, the used floss 16 is pulled away from the prongs 4a and 4b at the end of the applicator. The user just needs to action the lever backward a few times to get a new part of fresh floss to be spanned between the prongs of the applicator. The lever is brought back to its neutral position thanks to spring 24 and spring/pin 26 in the sliding mechanism. It has to be noted that spring strength of spring 24 is far stronger than spring 26. Device 26 allows shaft 22 to slide away from rack 23 which in turn moves up and disengages itself from the teeth of gearwheel 21 before reaching its resting position The used floss spool 21 can only rotate in one direction as a small blocking mechanism 38 prevents it from unreeling. FIGS. 4 and 5 show a fully electrical self-dispensing floss applicator according to a second embodiment of the present invention to provide ultimate user-friendliness and easy dispensing of floss. The inventive applicator is a combination of a light ergonomic applicator and a stable compact electrical base. In order to fully control the movement of floss between teeth and avoid hurting gums, it is critical that the applicator be as light, user-friendly and ergonomic as possible.

The incorporation of an electrical motor, a gear box and a set of batteries in the applicator itself would create a heavy, unbalanced and bulky applicator. Such characteristics would make it very difficult and almost impractical for the user to floss safely and effectively.

The electrically driven applicator of FIGS. 4 and 5 has essentially a similar design as the mechanical version described above according to FIGS. 1 to 3. The main difference is that lever 6 needs only to perform the locking function and, as such the sliding dispensing mechanism is not needed. The used floss reel 18 incorporates a large gearwheel that allows it to be set in rotary motion from outside the casing.

Figure 6:
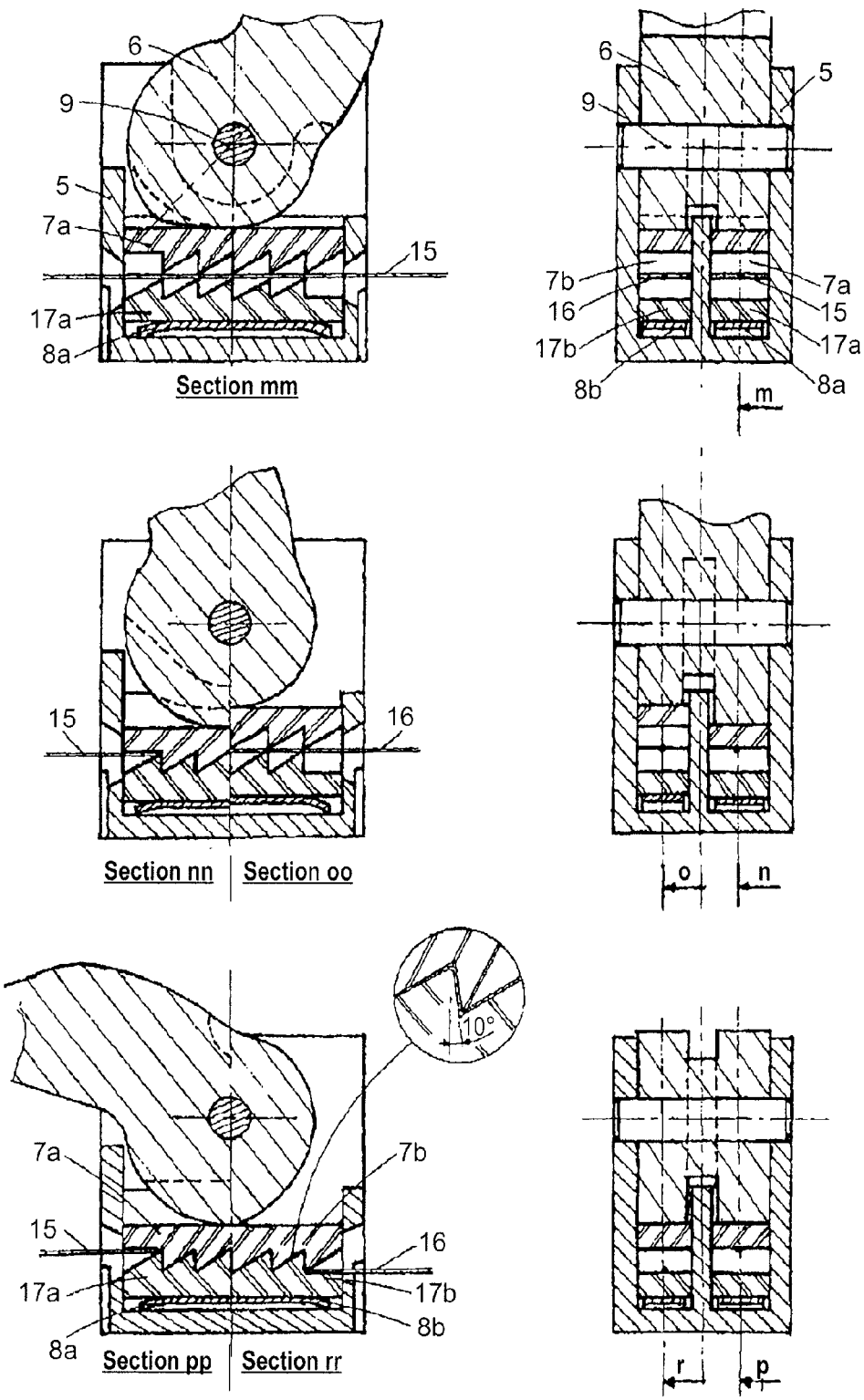
FIG. 6 shows details of the locking mechanism of the inventive self-dispensing dental floss applicator.

FIG. 6 shows details of the locking mechanism of the inventive dental floss applicator in different sectional views. Sectional view mm shows the lever 6 in an open position, perpendicular to the housing 1, where both fresh floss 15 and used floss 16 are free to move such that floss dispensing is performed. The free movement of the floss is possible since the both elements 7a, 17a including the saw-teeth have a certain distance such that the floss is free to move.

Sectional view nn and sectional view oo show the lever in a 45 degree position where fresh floss 15 is locked (sectional view nn), while the used floss 16 is being tensioned (sectional view oo) by the dispensing mechanism.

Sectional view p and sectional view rr show the lever 6 in the final locked position, alligned with housing 1. The sections pp and rr show fresh floss 15 and used floss 16 totally locked under pressure exercised by lever 6 on grid pads 7a and 7b and by springs 8a and 8b on grip pads 17a and 17b respectively.

A compact base 27 contains the electrical motor, the gearbox and the set of two e.g. AA batteries. By holding vertically and pressing down the unlocked applicator in the cavity located at the top of the base 27, a small micro switch 32 activates the electrical motor, which in turn sets the double gearwheel 33 in rotary motion. A positioning groove 37 that receives shape 38 ensures the applicator is placed properly on the base. The used floss spool 18 in the applicator is set in rotary motion and the flossed is dispensed rapidly. The user just needs to press the lever 6 forward in locked position while the floss is dispensed electrically by the base. The key feature here is the speed and ease at which dispensing of floss is made. Here again, the extra tautness feature 19 exists according to one inventive embodiment. The applicator is ready for use.

One of the great advantages of such design is that a family does not need as many electrical bases as they need applicators. One base per bathroom is enough as it can be used by many applicators. Additionally, 1.5 Volt AA batteries can be of a disposable or rechargeable nature. The base is compact enough to accompany the user during trips away from home. The base also plays the role of applicator stand when not in use.

Figure 7:
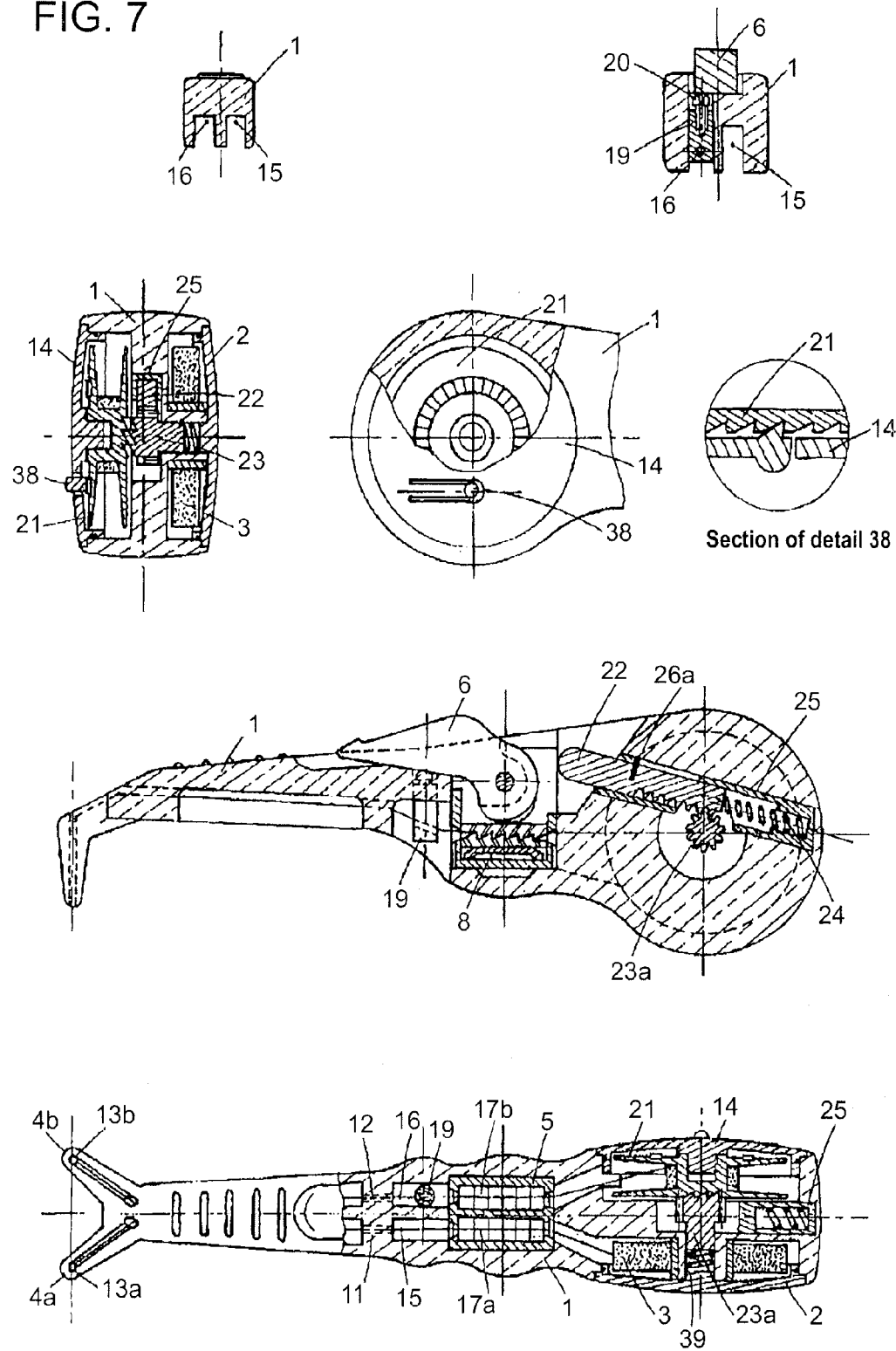
FIG. 7 shows details of a third embodiment of the inventive applicator.

The invention relates to a self-dispensing dental floss applicator that has a U-shaped elongated housing 1 with two hollow prongs 4a, 4b set perpendicularly to the body at one end and a larger opposite end to contain the locking mechanism, the dispensing mechanism, the spool 3 of fresh floss and the spool 18 and/or 21 of used floss. The locking mechanism composed of a casing 5, an axle 9, two lower grip pads 17a, 17b, two upper grip pads 7a, 7b, two strip springs 8a, 8b and a lever 6 with two eccentric friction parts is used to hold the floss in position thus creating the right tension on the floss. According to an embodiment of the invention, a tension pin 19 containing a screw 20 is provided to increase floss tension if/when needed by the user. Rotating the lever 6 up unlocks the floss. Further repeated rotations of the lever backward action the sliding mechanism containing a rack-and-pinion gear 23, 21, together with springs 24, 26, that in turn causes the spool of used floss 21 to rotate. Hence, new fresh floss is spanned between the prongs. In a separate embodiment, the applicator is placed on the electrical base and pressing it down will cause the spool of used floss 18 to rotate, hence pulling new fresh floss between the prongs in a very fast and easy manner. Pushing back the lever 6 to its locked position ensures the floss is tightly locked with the right tension. FIG. 7 shows a third embodiment of the present invention, which differs from the first embodiment shown in FIGS. 1 to 3 in that the used floss spool 21 is provided with a cogged part 23a which acts as a clutch. Thus, the gear wheel of the used floss spool 21 can remain in constant engagement with the toothed rack 23 during the forward and backward movement of the lever 6, as the clutch ensures that the used floss spool 21 only turns in the direction in which used floss is wound up onto the spool.

A helical spring 39 creates the required pressure on the clutch gear wheel 21, 23a so that rotational movement is transmitted to the spool 21 in order to wind up used floss and so that the cogged part 23a is released when the piston 22 returns to its resting position under pressure of the spring 24. A retention pin 26a prevents the piston 22 from moving out of the dispensing mechanism casing 25 during its linear motion.

Figure 8:
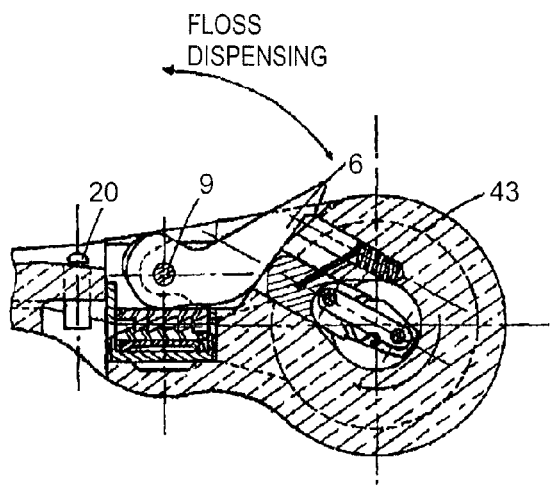
FIG. 8 shows details of a fourth embodiment of the inventive applicator.
Figure 8:
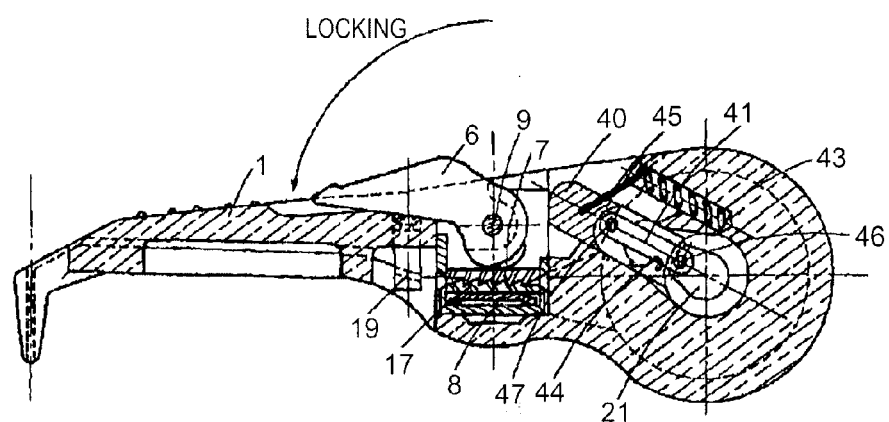
Figure 8:
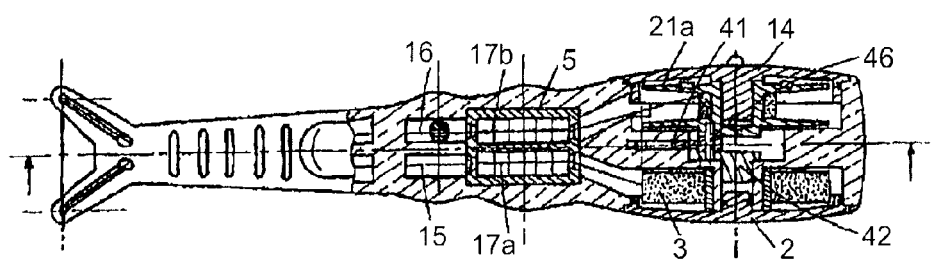

FIG. 8 shows a fourth embodiment of the present invention. In this embodiment, the backwards and forwards motion of the lever 6 is converted into rotational motion of the used floss spool 21a by means of a crankshaft arrangement, comprising a piston 40, a crankshaft 42, a connecting rod 41, a helical spring 43, a wire spring 44 and a retainer pin 45. The piston 40 is coupled to the connecting rod 41 via an axle pin 47 and the connecting rod 41 is coupled to the crankshaft 42 via an axle pin 46. The crankshaft 42 is formed integral with the used floss spool 21a.

Under backward movement of the lever 6, piston 40 transforms its linear movement into rotational movement of the crankshaft 42 via the connecting rod 41. As the crankshaft 42 completes the first half turn, the retainer pin 45 compresses the helical spring 43, which provides the necessary force to return the piston 40 to its original position once the lever 6 is back in the "locked" position. At the same time, the wire spring 44 provides the necessary force to push back the connecting rod 41 to its original position so that the used floss spool 21a rotates through 360 degrees.

Figure 9:
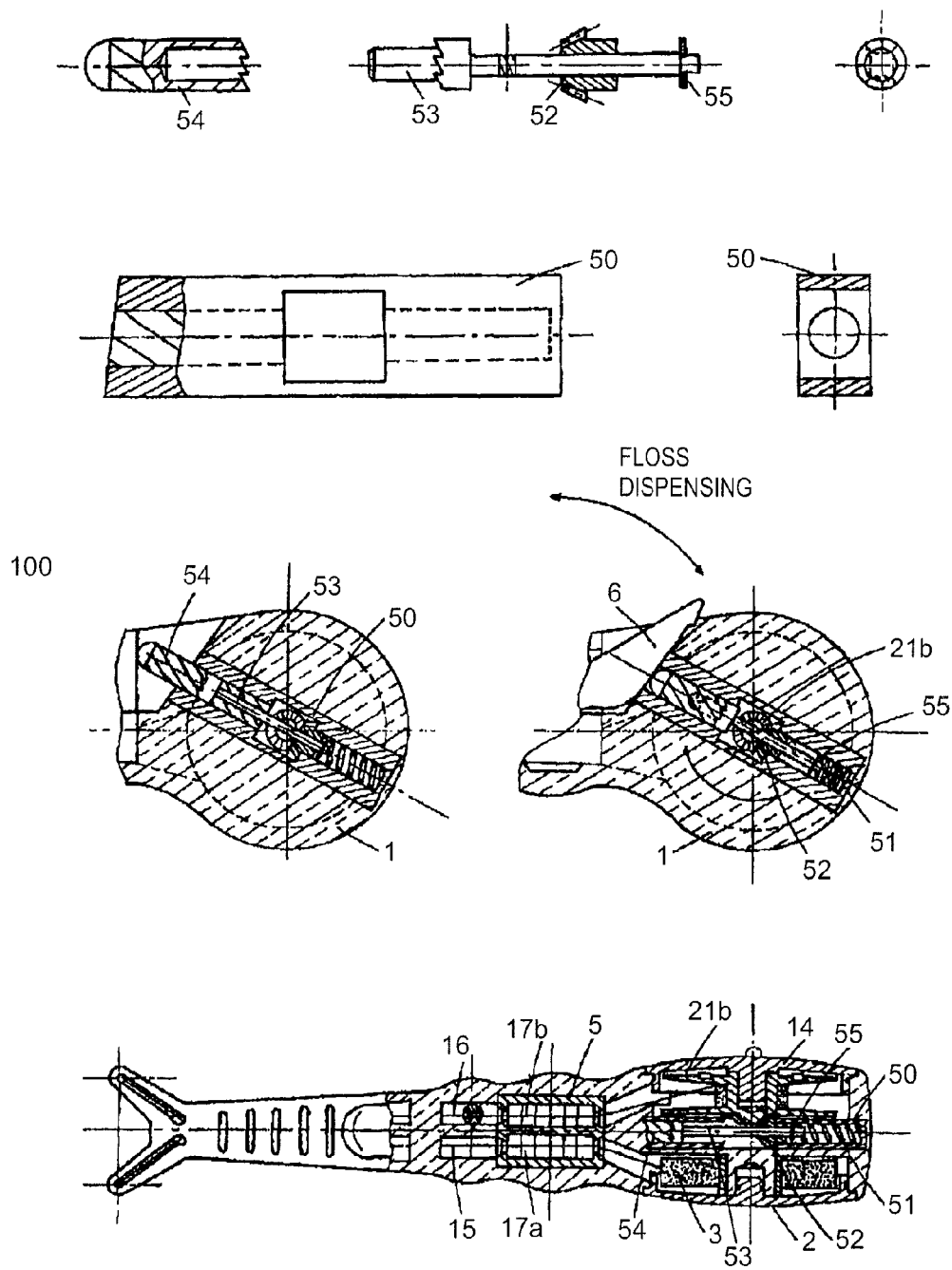
FIG. 9 shows details of a fifth embodiment of the inventive applicator.

FIG. 9 shows a fifth embodiment of the present invention. In this embodiment, the backward and forward motion of the lever 6 is converted into rotational motion of the used floss spool 21b by means of a helical piston 54 and a conical gearwheel 52.

All elements of the dispensing mechanism, comprising the helical piston 54, a connecting rod 53, the conical gear wheel 52 and a helical spring 51 are housed in a casing 50. The casing 50 is placed in a specially designed rectangular cavity in housing 1 before the used floss spool 21 is placed in housing 1 and maintained in position by cover 14. The conical gear wheel 52 is engaged with a conical gear wheel of the used floss spool 21b and is mounted on the connecting rod 53.

Under backward movement of lever 6, helical piston 54 is set into helical motion, which is converted into a rotational motion of the conical gear wheel 52 via the square section of connecting axle rod 53 passing through the conical gear wheel 52. Rotational motion of the conical gear wheel 52 is transmitted to the used floss spool 21b via the engagement of the conical gear wheels. After floss is dispensed, the helical spring 51 pushes against a stopper washer 55 mounted on the connecting rod 53 and thus provides the necessary force to push connecting rod 53 and piston back to their original positions when the lever 6 is back in the "locked" position.

The cogged end of connecting rod 53, as shown in the top part of FIG. 9, is designed to allow rod 53 to move back without rotation as the used floss spool 21b is prevented from unreeling by the anti-return device 38.

REFERENCES

1 U-shaped housing
2 fresh flosscap
3 fresh floss spool
4 hollow prong (a,b)
5 locking casing
6 double eccentric lever
7 upper grip pads (a, b)
8 curved strip spring (a, b)
9 lever axle
10 guiding partition
11 fresh floss bore
12 used floss bore
13 borings (a, b)
14 used floss cap
15 fresh floss
16 used floss
17 lower grip pads (a, b)
18 used floss spool
19 tension pin
20 screw
21 used floss spool
22 shaft
23 rack
24 spring
25 casing
26 spring
27 base
28 base cover
29 electrical motor
30 battery
31 battery cover
32 switch
33 gear wheel
34 holding part
35 screw
36 fastening means
37 positioning groove
38 anti-return device
26a retention pin
39 helical spring
40 piston
41 connecting rod
42 crankshaft
43 helical spring
44 wire spring
45 retainer pin
46 axle pin
47 axle pin
21a used floss spool with crankshaft arrangement
50 dispensing mechanism casing
51 helical spring
52 conical gear wheel
53 connecting axle rod
54 helical piston
55 stopper washer
21b used floss spool with conical gearwheel

The invention claimed is:

1. A self-dispensing dental floss applicator with a generally u-shaped housing having a space for a first spool of floss at its one end and two hollow prongs at its other end, the floss being spanned between the free ends of the two prongs and passed from the spool through a locking mechanism, a guiding section, the hollow prongs back through the guiding section and the locking mechanism, wherein the housing contains a second spool and that the first spool contains the fresh floss and that the second spool is for accumulating the used floss, wherein the second spool contains a gear wheel to drivingly connecting the gear wheel with a drive unit, wherein the applicator further comprises a tension pin, the position of which is adjustable by a screw in order to adjust the floss tension applied by the locking mechanism.

2. The self-dispensing dental floss applicator according to claim 1, wherein the locking mechanism consists of includes a casing rotatably mounting a double eccentric lever acting on two grip pads and locking the floss on the two grip pads under upward pressure of at least one spring.

3. The self-dispensing dental floss applicator according to claim 2, wherein the double eccentric lever exerts a pressure onto the grip pads in a direction perpendicular to the direction of movement of the floss.

4. The self-dispensing dental floss applicator according to claim 2, wherein the double eccentric lever is constructed such that, in a first position of the double eccentric lever, it acts on a first set of grip pads to lock the fresh floss supplied from the first spool, while a second set of grip pads allows the used floss to be tensioned by rotation of the second spool, and, in a second position of the double eccentric lever, it acts on both sets of grip pads to lock both the fresh floss and the used floss.

5. The self-dispensing dental floss applicator according to claim 1, wherein the floss spools of fresh and used floss are located in two separate compartments located in the housing closed by covers.

6. The self-dispensing dental floss applicator according to claim 5, wherein the floss spools are not in direct contact with any part of the human body while the self-dispensing floss applicator is in normal use for flossing.

7. The self-dispensing dental floss applicator according to claim 1, wherein the drive unit comprises a rack with gear teeth slidingly accommodated in a cavity of the housing such that the gear wheel meshes the rack with gear teeth.

8. The self-dispensing dental floss applicator according to claim 7, wherein the rack is in connection with a shaft, which can be operated with a lever.

9. The self-dispensing dental floss applicator according to claim 7, wherein the rack is biased by a spring such that the spring exercises a longitudinal force along its axis pushing the rack forward.

10. The self-dispensing dental floss applicator according to claim 8, wherein the shaft and lie rack are connected by a spring element.

11. The self-dispensing dental floss applicator according to claim 1, wherein the housing contains an opening in a rear end thereof for allowing a driving gear wheel to be introduced therethrough mesh the gear wheel within the housing.

12. The self-dispensing dental floss applicator according to claim 1, wherein the drive unit comprises a crankshaft arrangement comprising a crankshaft formed integrally with the second spool and driven by a piston.

13. The self-dispensing dental floss applicator according to claim 1, wherein the drive unit comprises a conical gear wheel arrangement, wherein a conical gearwheel is adapted to be driven by the helical motion of a helical piston and is in engagement with a further conical gear wheel formed integrally with the second spool.

14. An apparatus comprising a base element for a self-dispensing dental floss applicator with a generally u-shaped housing having a space for a first spool of floss at its one end and two hollow prongs at its other end, the floss being spanned between the free ends of the two prongs and passed from the spool through a locking mechanism, a guiding section, the hollow prongs back through the guiding section and the locking mechanism, wherein the housing contains a second spool and that the first spool contains the fresh floss and that the second spool is for accumulating the used floss, wherein the second spool contains a gear wheel to drivingly connecting the gear wheel with a drive unit, wherein the applicator further comprises a tension pin, the position of which is adjustable by a screw in order to adjust the floss tension applied by the locking mechanism, wherein the driving gear wheel is part of the base element.

15. The apparatus of claim 14, wherein said base element further comprises an electric motor, at least one battery and a switching element to start or stop the electric motor.

16. The apparatus of claim 15, wherein the switching element is a micro switch to be operated by introducing the rear end of the applicator into a recess of the base.

17. The apparatus of claim 15, said base element further comprising a guiding element in operational connection with an element of the housing of the applicator.

18. The apparatus of claim 17, wherein the guiding element is a positioning groove.

\* \* \* \* \*